United States Patent
Jones et al.

(10) Patent No.: US 8,152,814 B2
(45) Date of Patent: Apr. 10, 2012

(54) SEPARATOR TOOL FOR A MODULAR PROSTHESIS

(75) Inventors: Michael C. Jones, North Webster, IN (US); David K. DeBoer, Franklin, TN (US)

(73) Assignee: DePuy Products, Inc., Warsaw, IN (US)

( * ) Notice: Subject to any disclaimer, the term of this patent is extended or adjusted under 35 U.S.C. 154(b) by 1345 days.

(21) Appl. No.: 11/242,118

(22) Filed: Sep. 30, 2005

(65) Prior Publication Data

US 2007/0078464 A1 Apr. 5, 2007

(51) Int. Cl.
*A61F 2/46* (2006.01)
*A61B 17/92* (2006.01)

(52) U.S. Cl. .................................... 606/99; 606/86 R

(58) Field of Classification Search .............. 606/90, 606/99, 86 R; 623/22, 22.4, 22.42, 23.11
See application file for complete search history.

(56) References Cited

U.S. PATENT DOCUMENTS

| | | | |
|---|---|---|---|
| 3,541,868 A | 11/1970 | Hall | |
| 3,749,365 A * | 7/1973 | Van Gompel | 254/104 |
| 3,801,989 A | 4/1974 | McKee | |
| 4,457,306 A | 7/1984 | Borzone | |
| D290,399 S | 6/1987 | Kitchens | |
| 4,686,971 A | 8/1987 | Harris et al. | |
| 4,830,147 A * | 5/1989 | Kawada | 187/205 |
| 5,016,858 A * | 5/1991 | Mitchell | 254/45 |
| 5,049,150 A | 9/1991 | Cozad | |
| 5,061,271 A * | 10/1991 | Van Zile | 623/23.35 |
| D337,639 S | 7/1993 | Beckman | |
| 5,405,404 A | 4/1995 | Gardner et al. | |
| 5,476,466 A | 12/1995 | Barrette et al. | |
| 5,735,857 A | 4/1998 | Lane | |
| 5,849,015 A | 12/1998 | Haywood et al. | |

(Continued)

FOREIGN PATENT DOCUMENTS

DE 30 23 942 1/1982

(Continued)

OTHER PUBLICATIONS

"S-ROM Modular Hip System", retrieved from Johnson & Johnson Gateway web site http://www.jnjgateway.com/home.jhtml?loc=USENG&page=viewContent&contented=fc0de0010000030, retrieved on Sep. 26, 2005, 1 page.

(Continued)

*Primary Examiner* — Thomas C. Barrett
*Assistant Examiner* — Christopher Beccia
(74) *Attorney, Agent, or Firm* — Maginot, Moore & Beck

(57) ABSTRACT

A tool for separating components of a modular prosthesis includes an upper and lower body, each defining opposing bills at one end that are sized to fit in juxtaposed relation within an initial gap between the components. The upper body is provided with a handle so that the tool may be manually held by the surgeon with the opposing bills in position in the prosthesis. The tool includes a jack assembly disposed between the upper and lower bodies of the tool that is configured to be driven into an extended position, gradually separating the upper and lower bodies, and consequently exerting a separation force on the prosthesis components through the bills of the tool. The jack assembly is driven by a threaded actuator rod that bears against one element of the jack assembly as the actuator rod is rotated within a threaded bore in one of the bodies of the tool.

20 Claims, 3 Drawing Sheets

U.S. PATENT DOCUMENTS

| | | | | |
|---|---|---|---|---|
| 5,938,701 | A | 8/1999 | Hiernard et al. | |
| 6,013,082 | A | 1/2000 | Hiernard et al. | |
| 6,063,123 | A | 5/2000 | Burrows et al. | |
| 6,187,012 | B1* | 2/2001 | Masini | 606/99 |
| 6,238,435 | B1 | 5/2001 | Mculink et al. | |
| 6,319,286 | B1 | 11/2001 | Fernandez et al. | |
| 6,488,713 | B1 | 12/2002 | Hershberger | |
| 6,613,091 | B1 | 9/2003 | Zdeblick et al. | |
| 6,706,072 | B2 | 3/2004 | Dwyer et al. | |
| 6,712,825 | B2* | 3/2004 | Aebi et al. | 606/90 |
| 6,755,841 | B2* | 6/2004 | Fraser et al. | 606/99 |
| 6,840,944 | B2* | 1/2005 | Suddaby | 606/105 |
| 6,911,048 | B2 | 6/2005 | Fernandez et al. | |
| 7,189,242 | B2* | 3/2007 | Boyd et al. | 606/90 |
| 7,204,851 | B2* | 4/2007 | Trieu et al. | 623/17.11 |
| 7,387,635 | B2* | 6/2008 | Keller | 606/99 |
| 7,431,723 | B2* | 10/2008 | Hazebrouck | 606/99 |
| 2002/0004684 | A1 | 1/2002 | Thomas et al. | |
| 2003/0225416 | A1* | 12/2003 | Bonvallet et al. | 606/105 |
| 2004/0010262 | A1 | 1/2004 | Parkinson et al. | |
| 2004/0236342 | A1* | 11/2004 | Ferree et al. | 606/102 |
| 2005/0209597 | A1 | 9/2005 | Long et al. | |
| 2005/0234559 | A1 | 10/2005 | Fernandez et al. | |
| 2006/0058810 | A1 | 3/2006 | Wozencroft et al. | |
| 2007/0078464 | A1* | 4/2007 | Jones et al. | 606/86 |
| 2007/0260315 | A1* | 11/2007 | Foley et al. | 623/17.12 |
| 2008/0077156 | A1* | 3/2008 | Emstad | 606/105 |
| 2008/0114367 | A1* | 5/2008 | Meyer | 606/90 |
| 2008/0275457 | A1* | 11/2008 | Meek et al. | 606/99 |

FOREIGN PATENT DOCUMENTS

| | | |
|---|---|---|
| DE | 100 14 401 | 6/2001 |
| DE | 202006000845 | 4/2006 |
| EP | 0 333 990 | 9/1989 |
| EP | 0728449 B1 | 7/2002 |
| EP | 1191906 B1 | 6/2005 |
| FR | 2606628 | 5/1988 |
| FR | 2 850 563 | 8/2004 |
| WO | 0167997 | 9/2001 |
| WO | WO 2004/089224 | 10/2004 |

OTHER PUBLICATIONS

Zimmer®, Fracture Equipment and Orthopedic Appliances, 1 page.

EPO Search Report for EPO Application 06255071.0-1526, Dec. 28, 2007 (2 pages).

EPO Search Report for EPO Application 08167777.5-1526, Feb. 17, 2009 (2 pages).

Zimmer, Metasul LDH Large Diameter Head Surgical Technique, Enhancing Stability and Increasing Range of Motion (19 pages).

Zimmer®, Fracture Equipment and Orthopedic Appliances (1 page), published at least as early as Sep. 29, 2005.

* cited by examiner

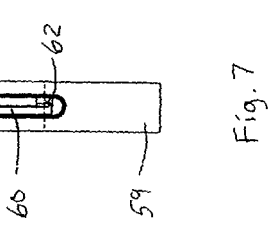
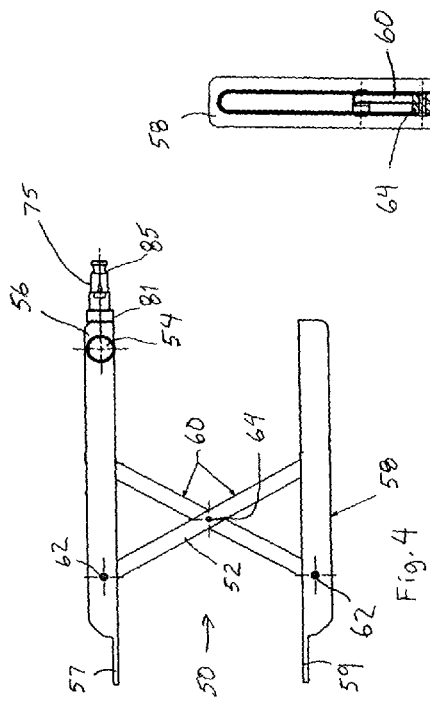
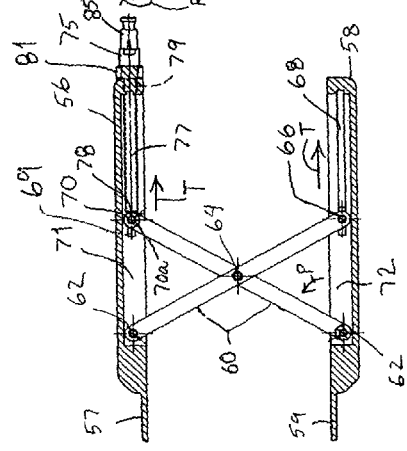
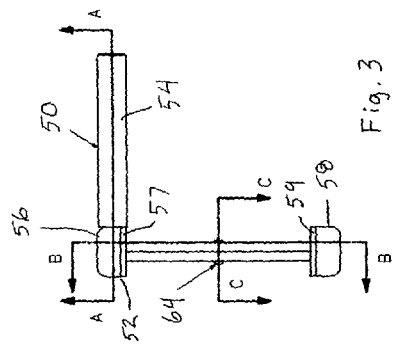
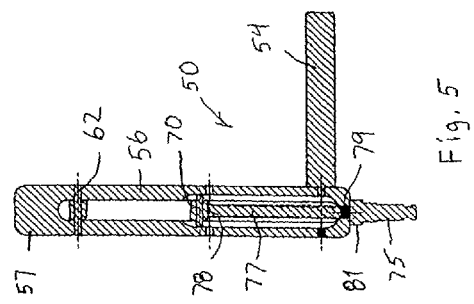

SEPARATOR TOOL FOR A MODULAR PROSTHESIS

TECHNICAL FIELD OF THE INVENTION

The present invention relates generally to modular orthopaedic prostheses, and more particularly to a tool for separating components of a modular prosthesis in situ.

BACKGROUND OF THE INVENTION

During the lifetime of a patient, it may be necessary to perform a joint replacement procedure to address damage to the joint due to, for example, disease or trauma. The joint replacement procedure may involve the use of a prosthesis which is implanted into at least one of the patient's bones. In the case of a hip replacement procedure, a femoral prosthesis is implanted into the patient's thigh bone or femur. The femoral prosthesis had been typically constructed as a one-piece structure having an upper portion that includes a spherically-shaped head which bears against the patient's pelvis or acetabulum, along with an elongated intramedullary stem which is utilized to secure the femoral component to the femur. In order to secure this prosthesis to the patient's femur, the medullary canal of the patient's femur is first surgically prepared (e.g. reamed and/or broached) such that the intramedullary stem of the femoral prosthesis may be subsequently implanted therein. The femoral prosthesis may be press fit into the medullary canal or, in the alternative, bone cement may be utilized to secure the femoral prosthesis within the medullary canal.

During performance of a joint replacement procedure, it is generally desirable to provide the surgeon with a certain degree of flexibility in the selection of a prosthesis. In particular, the anatomy of the bone into which the prosthesis is to be implanted may vary somewhat from patient to patient. For example, in the case of a femoral prosthesis, the patient's femur may be relatively long or relatively short thereby requiring use of a femoral prosthesis which includes a stem that is relatively long or short, respectively. Moreover, in certain cases, such as when use of a relatively long stem length is required, the stem must also be bowed in order to conform to the anatomy of the patient's femur. The trochanteric region of the femur may require a specially sized proximal portion of the prosthesis or a particular angle of the proximal portion to mate with the articulations of the hip joint.

Such a need for prostheses of varying shapes and sizes created a number of problems in regard to use of a one-piece prosthesis. As a result of these problems, the modular prosthesis was developed. As the name implies, a modular prosthesis is constructed in modular form so that the individual elements or features of the prosthesis can be selected to fit the needs of a given patient's anatomy. Examples of certain modular prostheses are found in U.S. Pat. No. 6,706,072 (the '072 Patent), issued to DePuy Orthopaedics, Inc., including the two prosthesis illustrated in FIGS. 1-2. In general, the modular femoral prosthesis, such as the prosthesis 10 of FIG. 1, includes a proximal neck component 12 that includes a body 24 that terminates in a trunnion 26 onto which a variety of head bearing components (not shown) that mate with the patient's natural acetabulum or to a prosthetic socket.

The neck component 12 fits within a sleeve 14 that is configured to fit within a surgically prepared end of the femur. In a joint replacement procedure, the head of the natural femur is removed to form a flat surface across the trochanters of the femur. The medullary canal of the femur is reamed and/or broached and a cavity is formed in the proximal prepared end of the bone to receive the sleeve 14. The sleeve component 14 may be provided in carrying angles and lengths to fit the needs of the patient's joint anatomy. A distal stem component 18 is provided that is implanted within the prepared medullary canal. As indicated above, the stem component 18 may be provided in various sizes and curvatures to accommodate the anatomy of the particular femur.

All of the components of the modular prosthesis are configured to be rigidly engaged when the prosthesis 10 is implanted. Thus, the prosthesis 10 described in the '072 Patent includes a tapered shank 13 projecting from the body 24 of the proximal neck component 12. The shank 13 extends into a tapered bore 30 of the sleeve 14 in a press-fit engagement. The two tapered elements (shank 13 and bore 30) may define a Morse taper for rigid fixation between the sleeve and neck component. The shank 13 also defines a tapered bore 22 for a press-fit engagement with a tapered post 19 of the distal stem component 18. The end of the post 19 may be provided with threads 28 to be threaded into mating threads 29 in the shank 13 of the proximal neck component 12.

A modified prosthesis 10' is shown in FIG. 2. This modified prosthesis includes a sleeve 14 that is substantially the same as the sleeve shown in FIG. 1. The proximal neck component 12' is similar to the neck component 12 in that includes a tapered shank 13' for press-fit engagement within the mating bore of the sleeve 14. However, the bore 22' of the neck component 12' extends entirely through the component. The distal stem component 18' of FIG. 2 is similar to the stem component 18 of FIG. 1, except that the tapered post 19' is longer and terminates in a threaded end 28' that is configured to be engaged by a threaded nut or cap 29'.

With either prosthesis 10 or 10', the head of the femur is prepared as described above and the sleeve 14 pressed into the prepared proximal end. Bone cement may be used to help fix the sleeve 14 within the bone. The distal stem component 18/18' is introduced through the sleeve bore 30 into the prepared medullary canal of the femur. The proximal neck component 12/12' is then positioned with the sleeve bore 30 and advanced into the bore so that the tapered bore 22/22' fits over the tapered post 19/19' of the distal stem component. The threaded end 28/28' is threaded into the appropriate mating component for the two prostheses 10/10'. One concern that has arisen with modular prostheses is the locking of the components relative to one another. The fixation of the distal stem component 18/18' to the proximal neck component 12/12' and of the neck component to the sleeve 14 in the prostheses 10/12' of FIGS. 1-2 address this concern. This fixation among the components allows the components to adequately absorb the axial functional loads exerted on the prosthesis without appreciable degradation or even breach of the mechanical integrity prosthesis. Ideally, the functional loads on these prostheses 10/10' increase or improve the self-locking attributes of the devices.

In some joint replacements a revision of the prosthesis may be necessary. For instance, in some cases, a distal stem component is implanted that has a version that is determined to be less than optimal for the anatomy of the patient's femur. In other cases, the proximal neck component or distal stem requires replacement due to wear or damage, or because of changes in the patient's joint anatomy that can occur over time. At any rate, the otherwise beneficial self-locking characteristics of the modular prostheses 10/10' become a disadvantage in a revision procedure where it is necessary to separate the neck and stem components from the stable well-fixed sleeve.

The current method of removing the neck and stem components from the sleeve is to use a bone chisel to wedge between the proximal surface 16 of the sleeve 14 and the opposing surface 25 of the neck component 12/12' (FIG. 1). A bone chisel is initially pushed into the space between the two surfaces 16, 25 to incrementally disassociate the components from the sleeve. When the gap is large enough, a second bone chisel is introduced into the space, and so on with multiple chisels until the gap is large enough to accept an impaction tool. The distal surface 25 of the neck component 12/12' is impacted until it is dislodged from the sleeve.

This technique suffers from a few problems. Foremost is the inherent difficulties associated with using a bone chisel to wedge fixed components apart. The chisel may slip out of place and damage surrounding tissue or cut through the surgeon's gloves. In addition, the use of an impaction tool to separate the components from the sleeve tends to produce an axial load on the sleeve that can tend to disassociate the sleeve from the proximal end of the femur.

Consequently, there is a need for a tool that can be used to remove the neck and stem components of a modular prosthesis from the sleeve, while keeping the sleeve intact within the prepared bone.

SUMMARY OF THE INVENTION

In order to address this need, a tool is provided that permits separation of fixed components of a modular prosthesis without the need for use of a bone chisel and an impaction tool. The tool of one embodiment of the invention allows for the application of uniform pressure against both the sleeve and the component to be removed to gradually increase the gap between the modular components. The tool may be used in virtually any orientation without requiring undue manipulation of the patient's joint.

In one feature of the invention, the separation tool includes an upper and lower body, each defining opposing bills at one end that are sized to fit in juxtaposed relation within an initial gap between components of a modular prosthesis. In the case of a modular hip prosthesis, the juxtaposed bills fit in the gap between the sleeve and the proximal neck component. The upper body is provided with a handle extending outwardly from the body so that the tool may be manually held by the surgeon with the opposing bills in position in the prosthesis.

In a further feature of the invention, a jack assembly is disposed between the upper and lower bodies of the tool. Preferably the jack assembly is configured to be contained within cavities formed in the upper and lower bodies when the jack is in its retracted or un-extended orientation. The jack assembly is configured to be driven into an extended position, gradually separating the upper and lower bodies, and consequently exerting a separation force on the prosthesis components through the bills of the tool. In one preferred aspect, the jack assembly is driven by a threaded actuator rod that bears against one element of the jack assembly as the actuator rod is rotated within a threaded bore in one of the bodies of the tool.

In the preferred embodiment, the jack assembly is a scissors jack with crossed arms pivotably mounted at one end to a corresponding body and pivotably connected to each other at a mid-length position on each arm. The opposite ends of the arms are movably disposed within an opposite body (i.e., one arm is pivotably mounted to the upper body and slidably disposed in the lower body). The opposite end of at least one of the arms includes a pin that travels within a slot formed in one body to restrain the end of the arm to linear motion. Preferably, the non-pivotably mounted ends of both arms are similarly restrained to linear movement. The moving end of one arm may include a bushing to bear against the end of the threaded rod. Thus, in the operation of the tool, the threaded rod is threaded into the tool body to push against the bushing of the end of one arm. As that arm is pushed toward the opposite end of the body, the linkage formed by the pivot mounts and pivot connection between the arms causes the opposite arm to travel in the same manner.

Thus, the translating ends of the arms of the scissors jack move simultaneously toward the pivoting ends of the arms, thereby shortening the axial extent of the scissors jack while increasing the transverse or vertical height of the jack. It is this increase in vertical height that forces the upper and lower bodies, and ultimately the upper and lower bills, apart. Preferably, the proximal end of the threaded actuator rod includes a fitting for engagement with a driving tool. The driving tool may be manually operated, such as a crank, socket wrench or T-handle, but may instead be electrically or pneumatically powered.

It is one object of the invention to provide a tool that is operable to separate components of a modular prosthesis in situ. A further object of the invention is achieved by features that allow this separation to occur without compromising the integrity of components that are intended to remain within the bone or joint.

One benefit of the separation tool of the present invention is that it provides for controlled application of force between the components being separated. Another benefit is that the tool itself has a minimal profile so that it is not cumbersome to use and so that it does not interfere with the components of the prosthesis or the surrounding tissue. Other benefits and objects of the invention will become apparent upon consideration of the following written description taken together with the accompanying figures.

DESCRIPTION OF THE FIGURES.

FIG. 3 is a top elevational view of a separation tool according to one embodiment of the present invention.

FIG. 4 is a side elevational view of the separation tool shown in FIG. 3 with the tool depicted in its expanded configuration.

FIG. 5 is a cross-sectional view of the tool shown in FIG. 3, taken along line A-A as viewed in the direction of the arrows.

FIG. 6 is a cross-sectional view of the tool shown in FIG. 3, taken along line B-B as viewed in the direction of the arrows.

FIG. 7 is a cross-sectional view of the tool shown in FIG. 3, taken along line C-C as viewed in the direction of the arrows.

DESCRIPTION OF THE PREFERRED EMBODIMENTS

Figure 1:
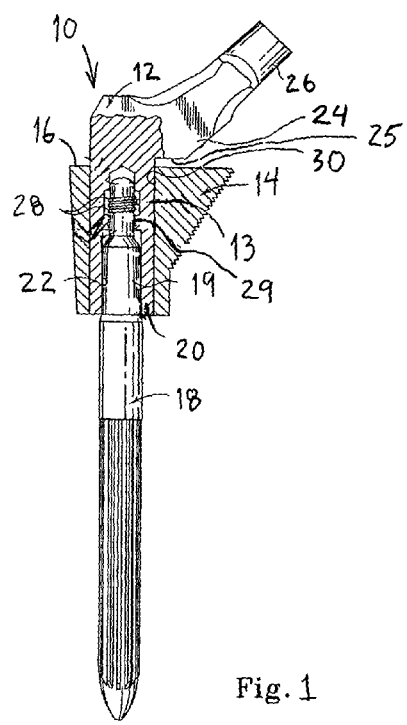
FIG. 1 is a side partial cut-away view of a modular hip prosthesis that may be disassembled by the separation tool of the present invention.
Figure 2:
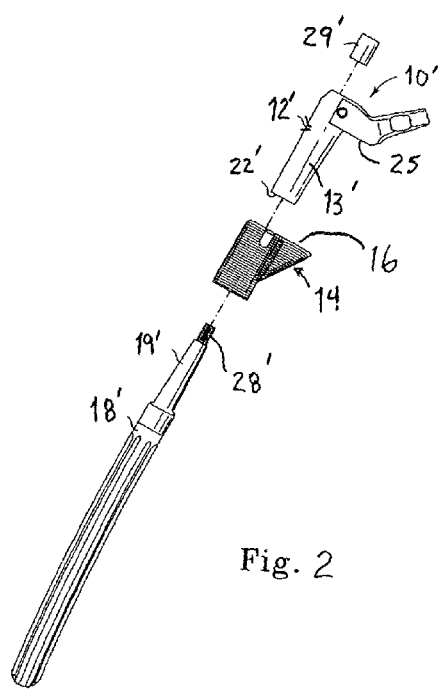
FIG. 2 is an exploded perspective view of an alternative modular hip prosthesis that may be disassembled by the separation tool of the present invention.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

In accordance with one embodiment of the invention, a separation tool 50 is provided that includes a pair of separator bodies 56, 58 connected by and separable by a jack assembly 52, as shown in FIGS. 3-6. The jack assembly 52 is operable to move the upper body 56 and the lower body 58 between an expended position depicted in FIG. 4 and a contracted, or insertion, position shown in FIG. 8. The upper body 56 is provided with a handle 54 extending generally perpendicularly outward from the body. The handle is sized to be manually grasped by the surgeon to facilitate insertion of the tool into the joint space and to stabilize the tool while it is being used to separate the implant components. In a specific embodiment, the handle 54 includes a knurled outer surface, and has a length of about 90 mm and a diameter of about 14 mm.

Figure 8:
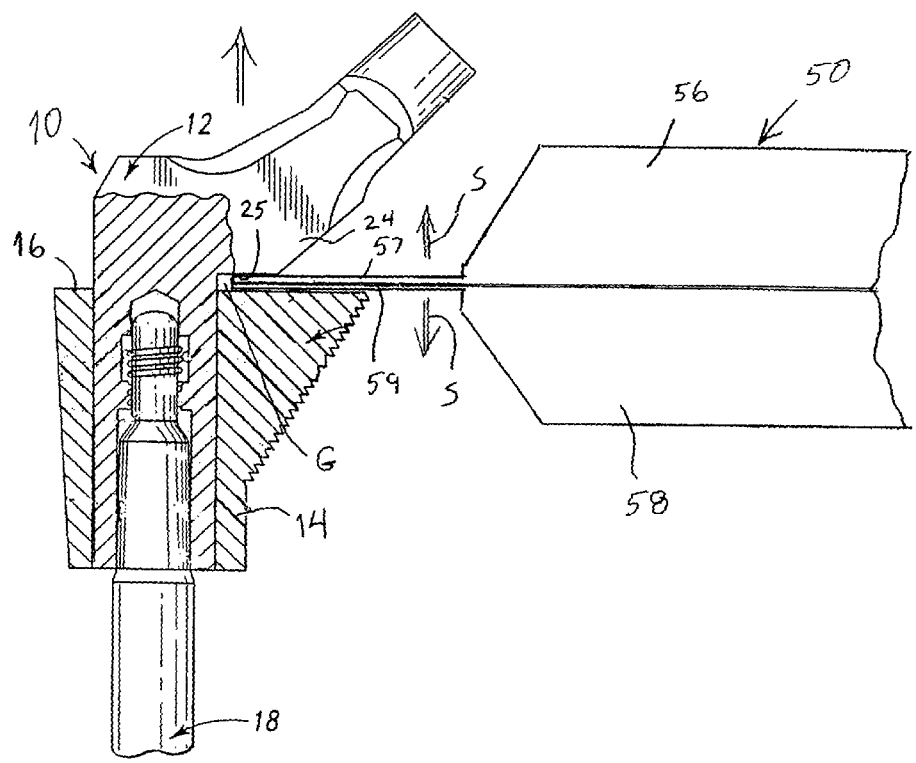
FIG. 8 is an enlarged partial cross-sectional view of the separation tool depicted in FIG. 3 being used to separate components of the modular hip prosthesis illustrated in FIG. 1.

One end of each separator body 56, 58 includes a corresponding bill 57, 59 extending along the longitudinal axis of the body. The bills 57, 59 are sized so that when the bills are juxtaposed, as depicted in FIG. 8, they can fit in the gap G between the proximal surface 16 of the sleeve 14 and the opposite surface 25 of the neck component 12. The length of the bills 57, 59 from the end of the tool bodies is also sufficient to access the gap G in the joint prosthesis while the separator bodies are not impeded by the prosthesis or surrounding joint tissue. In a specific embodiment, the bills 57, 59 have a length from the end of each body 56, 58 of about 25 mm. In this specific embodiment, the thickness of each bill is about 2.54 mm so that their combined juxtaposed thickness is about 5.08 mm, which is sufficiently thin to fit within the gap G of most implanted prostheses. The separator bodies 56, 58 are further sized so that the handle 54 is accessible to be grasped outside the surgical site. In this illustrated embodiment, the bodies have a length of about 162 mm and may be provided with an angled surface leading to each bill to increase clearance around the prosthesis.

The operating mechanism of the separator tool 50 is a jack assembly 52 that operates to separate the bodies 56, 58. In the preferred embodiment, the jack assembly includes a pair of arms 60 that are arranged in a crossed configuration, as shown in FIGS. 4 and 6. One end of each arm 60 is pivotably connected to a corresponding separator body at an end pivot mount. 62. The two arms are connected to each other at a center pivot 64 situated at mid-length of each arm. In the illustrated embodiment, the center pivot 64 is at the center of each arm 60 for the optimum stroke and mechanical advantage. While one end of each arm is restrained to pivot relative to the corresponding separator body, the opposite end is constrained to translate within the opposite separator body. Thus, the arm pivotably connected to the upper body 56 is connected to the lower body 58 by way of a pin 66 extending through an elongated slot 68 formed in that body, as shown in FIG. 6. The pin and slot constrain end of the arm 60 to translate within the lower separator body 58 in the direction T.

Similarly, the top separator body 56 defines a slot 69 that receives a pin 70a connected to the translating end of the arm that is pivotably connected to the lower body. The pin 70a preferably includes a bushing 70 that provides a bearing surface for contacting the actuator rod 75. In the preferred embodiment, the ends of the crossed arms 60 are contained within cavities 71, 72 defined in the two bodies 56, 58, respectively. The actuator rod 75 is also disposed in the cavity 71. The cavities allow the two bodies to contact flush as depicted in FIG. 8. Alternatively, the bills 57, 59 can be configured to achieve flush juxtaposition regardless of whether or not the upper and lower bodies 56, 58 are flush in their insertion configuration.

The actuator rod 75 includes a threaded stem 77 terminating in an end 78 that bears against the bushing 70. The threaded stem 77 is threaded into and out of a threaded bore 79 defined in the proximal end of the upper separator body 56. As the actuator rod 75 is threaded into the upper body, the end 78 of the stem 77 pushes on the bushing 70 causing the end of the arm 60 to translate along the slot 69. This movement results in a rotation P of the arm about the pivot mount 62 in the lower body 58, which in turn causes rotation of the other arm about the pivot mount in the upper body. The mechanism thus operates like a known scissors jack so that forced translation of one end of the linkage formed by the crossed arms cause the ends of the arms to approach each other. In so doing, the jack assembly increases the separation between the upper and lower bodies 56, 58, and ultimately the separation between the bills 57, 59. As the bills separate they contact and push against the surfaces 16 and 25 to drive the proximal neck component 12 away from the sleeve 14.

The length of the arms 60 are established to separate the prosthesis components far enough to be easily dislodged manually or by an impact tool if necessary. In a specific embodiment for separation of a neck component from a sleeve of a hip prosthesis, the arms have a length of about 115 mm between the pivot mount 62 and the corresponding pin 66, 70a. If the arms are pivoted to a substantially overlapping orientation, the stability of the tool is compromised. Thus, the amount of pivoting of the arms 60 is preferably limited, or more appropriately the amount of translation of the non-pivoting end is constrained by the length of the corresponding slot 68, 69. In the illustrated embodiment, the slots terminate about halfway into each body so that the overall travel of the arms in the slots is about 75% of the arm length. This results in a maximum expanded separation of about 75% of the arm length, or about 88 mm. The slots 68, 69 are further sized so that the arms 60 are fully contained within the cavities 71, 72, which corresponds to a slot length of about 78 mm.

It can be appreciated that the jack assembly 52 and the actuator rod 75 provide means for a controlled and smooth separation of the components of the prosthesis 10 or 10'. The thread pitch between the threaded stem 77 and the threaded bore 79 can be sized to achieve a determinate amount of translation or separation of the bodies 56, 58 with each degree of rotation of the actuator rod 75. In other words, a finer thread pitch will result in small changes in separation as the rod is rotated, while a larger pitch will produce greater separation movement with rod rotation.

The actuator rod 75 includes a stop 81 that is disposed outside the upper body 56 and serves to limit the depth of insertion of the threaded stem 77 into the upper body. The actuator rod further includes a fitting 85 that is configured for engagement by a driving tool that is operable to rotate the rod in the direction R. The fitting may be configured as a Hudson connection to mate with a T-handle that allows manual rotation of the rod. The fitting may also be configured to engage a crank arm, socket wrench or even a powered surgical driver. In the preferred embodiment, the mechanical advantage provided by the jack assembly 52 allows the use of a manually rotated T-handle to separate the press-fit components of a typical prosthesis.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

For instance, the illustrated embodiment of the separation tool is shown and described for use in separating components of a modular femoral prosthesis for the hip joint. The tool 50 may be used to separate modular components of other orthopaedic implants. The bills 57, 59 may be modified to engage appropriate surfaces of the components to be separated. In the illustrated embodiment, the bills 57, 59 may be modified to include a cut-out at the end of each bill that is sized to fit around a part of the shank 13 of the proximal neck component 12.

The tool is particular suited for modular implants where the tool can be introduced within a gap between the components and where it is desirable to maintain the position and stability of one of the components. Alternatively, the bills 57, 59 of the tool may be disposed within a gap between a prosthesis component and a prepared surface of a bone.

While the tool 50 is adapted for use in separating modular prosthesis components in situ, the tool may also be used outside the patient. In particular, the tool may be used to separate components that have been pre-assembled prior to implantation.

In the illustrated embodiment, the actuator rod 75 includes a threaded stem 77 that is rotated within a threaded bore 79 of the top separator body 56 to extend the rod into or retract the rod from within the cavity 71, and more particularly to push on or withdraw from the bushing 70 on the crossed arm 60. The threaded configuration optimizes the mechanical advantage to permit manual operation of the jack assembly. However, other actuator rod configurations are contemplated that produces linear movement of the rod end 78 to bear against the crossed arms to operate the jack assembly 52. For instance, the actuator rod may incorporate a rack and pinion drive arrangement, or a ratchet and trigger assembly. As a further alternative, the actuator rod may incorporate a pneumatic cylinder in which the piston extends to bear against the bushing.

What is claimed is:

1. A tool for separating two joined components of an orthopaedic prosthesis, said tool comprising:
    opposed bills including a first bill with a first outermost surface, the first outermost surface configured for pressing engagement with a surface of a first of the two joined components, and a second bill with a second outermost surface, the second outermost surface configured for pressing engagement with a surface of a second of the two joined components, said opposed bills being movable between (i) a first relative position in which said opposed bills are substantially juxtaposed to each other, and (ii) a second relative position in which said opposed bills are spaced apart from each other;
    opposed separator bodies including (i) a first body connected to said first bill, and (ii) a second body connected to said second bill; and
    a jack assembly disposed between said separator bodies and operable to move said separator bodies apart from a first configuration in which said separator bodies locate said opposed bills in said first relative position, and a second configuration in which said separator bodies locate said opposed bills in said second relative position,
    wherein said jack assembly includes a first arm having (i) a first end portion pivotably connected to said first body, and (ii) a second end portion slidably connected to said second body, and
    wherein the opposed bills are dimensioned such that when the opposed bills are in the first relative position, the opposed bills fit within a gap defined between two rigidly engaged components of an orthopaedic prosthesis that are to be separated.

2. The tool for separating two joined components of an orthopaedic prosthesis of claim 1, further comprising a handle projecting from at least one of said opposed separator bodies, said handle fixedly attached to said at least one of said opposed separator bodies and configured to be manually grasped to support said tool.

3. The tool for separating two joined components of an orthopaedic prosthesis of claim 1, further comprising:
    a second arm having (i) a third end portion pivotably connected to said second body, and (ii) a fourth end portion slidably connected to said first body,
    wherein said first arm and said second arm are pivotably connected to each other.

4. The tool for separating two joined components of an orthopaedic prosthesis of claim 1, further comprising:
    a threaded bore fixedly positioned with respect to the second separator body;
    a slot extending axially along the second separator body, the second end portion slidably guided by the slot; and
    a threaded rod meshingly engaged with said threaded bore and configured to move the second end portion.

5. The tool for separating two joined components of an orthopaedic prosthesis of claim 4, wherein:
    said threaded rod includes a first rod end portion that contacts said second end portion of said first arm, and (ii) an opposite second rod end portion that has a fitting configured for engagement by a driving tool operable to rotate said threaded rod.

6. The tool for separating two joined components of an orthopaedic prosthesis of claim 5, wherein said fitting is a Hudson connection.

7. The tool for separating two joined components of an orthopaedic prosthesis of claim 5, wherein said threaded rod further includes (i) a threaded stem, and (ii) a stop located between said fitting and said threaded stem, said stop configured to limit movement of said threaded rod with respect to said second separator body.

8. The tool for separating two joined components of an orthopaedic prosthesis of claim 1, wherein:
    said second body defines a first slot; and
    said second end portion includes a first pin extending therefrom and sized to be slidably received within said first slot.

9. The tool for separating two joined components of an orthopaedic prosthesis of claim 8, wherein:
    said jack assembly includes a second arm having (i) a third end portion pivotably connected to said second body, and (ii) a fourth end portion slidably connected to said first body;
    said first body defines a second slot; and
    said fourth end portion includes a second pin extending therefrom and sized to be slidably received within said second slot.

10. The tool for separating two joined components of an orthopaedic prosthesis of claim 2, wherein:
    the at least one of said opposed separator bodies defines a longitudinal axis; and
    the handle projects from the at least one of said opposed separator bodies substantially perpendicularly to the longitudinal axis.

11. The tool for separating two joined components of an orthopaedic prosthesis of claim 10, wherein:

the opposed bills are located forwardly of the opposed separator bodies along a longitudinal axis defined by the first body;

the at least one of said opposed separator bodies defines a slot extending along the longitudinal axis;

the second end portion includes a pin extending therefrom and sized to be slidably received within the slot; and the slot extends forwardly and rearwardly of the handle along the longitudinal axis.

12. The tool for separating two joined components of an orthopaedic prosthesis of claim 11, wherein:

the handle projects from the at least one of said opposed separator bodies at a location axially proximate to an end portion of the slot.

13. The tool for separating two joined components of an orthopaedic prosthesis of claim 1, wherein:

the orthopaedic prosthesis is configured such that the opposed bills contact each other in the first relative position.

14. The tool for separating two joined components of an orthopaedic prosthesis of claim 13, further comprising:

a cavity defined by the first body, wherein the first end portion is pivotably connected to the first body within the cavity.

15. The tool for separating two joined components of an orthopaedic prosthesis of claim 14, wherein the jack assembly is configured such that as the opposed bills move from the first relative position toward the second relative position, a portion of the first arm moves out of the cavity.

16. A tool for separating an orthopaedic component from a receptacle, the tool comprising:

a first separator body defining a longitudinal axis;

a second separator body extending along the longitudinal axis;

a first bill extending forwardly from the first separator body and including a first inward surface and a first outermost surface, the first outermost surface configured for pressing engagement with a third surface of the orthopaedic component;

a second bill extending forwardly from the second separator body and including a second inward surface and a second outermost surface, the second outermost surface configured for pressing engagement with a fourth surface defining an opening to the receptacle; and a jack assembly disposed between the first separator body and the second separator body and configured to move the first separator body and the second separator body between a first configuration in which the first inward surface and the second inward surface are proximate to each other and a second configuration in which the first inward surface and the second inward surface are spaced apart from each other, wherein the first bill and the second bill are dimensioned so as to fit within a gap between the orthopaedic component and the fourth surface when the orthopaedic component is rigidly engaged with the receptacle and the first separator body and the second separator are in the first configuration.

17. The tool of claim 16, wherein the jack assembly comprises:

a first arm having (i) a first end portion pivotably connected to the first separator body, and (ii) a second end portion slidably connected to the second separator body.

18. The tool of claim 17, wherein the jack assembly further comprises:

a second arm having (i) a third end portion pivotably connected to the second separator body, and (ii) a fourth end portion slidably connected to the first separator body.

19. The tool of claim 18, further comprising:

a first slot defined by the first separator body and extending along the longitudinal axis, the first slot including a rearward end portion; and a second slot defined by the second separator body and extending along the longitudinal axis, wherein:

the fourth end portion is slidably guided by the first slot;

the second end portion is slidably guided by the second slot;

the first arm has a first length; and the rearward end portion is configured to limit movement of the first bill away from the second bill to a distance that is about 75% of the first length.

20. The tool for separating components of an orthopaedic prosthesis of claim 17, further comprising:

a threaded bore fixedly positioned with respect to the second separator body;

a slot extending axially along the second separator body, the second end portion slidably guided by the slot; and a threaded rod meshingly engaged with said threaded bore and configured to move the second end portion.

* * * * *